US00PP16718P3

(12) United States Plant Patent
Munn

(10) Patent No.: US PP16,718 P3
(45) Date of Patent: Jun. 27, 2006

(54) *ACER SHIRASAWANUM* PLANT NAMED 'MUNN 001'

(50) Latin Name: *Acer shirasawanum*
Varietal Denomination: MUNN 001

(76) Inventor: Carl A. Munn, 9445-72nd Ave., Brooks, OR (US) 97305-9754

( * ) Notice: Subject to any disclaimer, the term of this patent is extended or adjusted under 35 U.S.C. 154(b) by 87 days.

(21) Appl. No.: 10/895,191

(22) Filed: Jul. 19, 2004

(65) Prior Publication Data

US 2006/0015976 P1 Jan. 19, 2006

(51) Int. Cl.
*A01H 5/00* (2006.01)

(52) U.S. Cl. ..... Plt./216
(58) Field of Classification Search ..... Plt./216, Plt./224
See application file for complete search history.

(56) References Cited

U.S. PATENT DOCUMENTS

PP10,590 P * 9/1998 Cole ..... Plt./224
PP11,119 P * 11/1999 Lamis ..... Plt./224

OTHER PUBLICATIONS

Eyre, S. N. ed. Sunset National Garden Book. Sunset Books, Inc. Menlo Park, CA 1997 pp. 164–166 "*Acer*".*

UPOV ROM GTITM Computer Database, GTI Jouve Retrieval Software 2005/02 Citations for 'MUNN 001'.*

* cited by examiner

*Primary Examiner*—Kent Bell
*Assistant Examiner*—W. C. Haas
(74) *Attorney, Agent, or Firm*—Klarquist, Sparkman, LLP

(57) ABSTRACT

A new and distinct cultivar of *Acer shirasawanum* plant as shown and described, characterized by its striking carmine to red spring leaves, yellow to lime summer leaves, and vigorous growth rate.

4 Drawing Sheets

Botanical classification: *Acer shirasawanum.*
Variety nomination: 'MUNN 001'.

The present invention relates to a new and distinct cultivar of deciduous tree of the genus and species, *Acer shirasawanum,* and given the name 'MUNN 001'. The genus *Acer* is of the family Aceraceae.

The new cultivar was found in a cultivated area by Carl Munn as a chance seedling of *Acer shirasawanum* 'Aureum', an unpatented plant.

*Acer shirasawanum* 'Aureum' is described in the A to Z Encyclopedia of Garden Plants as a "Rounded, bushy, deciduous tree or shrub producing rounded, 7 to 11-lobed, bright yellow leaves, 7–10 cm long. Tiny, red-purple flowers are borne in upright corymbs." *Acer shirasawanum* 'Aureum' is a problem for growers due to its slow growth. It is also difficult to propagate as it doesn't take a graft well. In addition, its leaves burn badly in full sun.

This new cultivar is characterized by the following:

1. Vigorous and fast and upright growing;
2. Carmine to red new growth in spring fading to gold in summer;
3. Sun tolerance, can be grown in full sun with only light burning on top leaves;
4. Lime green foliage where shaded.

Asexual propagation by side grafts in Brooks, Oreg., shows that the foregoing characteristics and distinctions come true to form and are established and transmitted through succeeding propagations. The present invention has not been evaluated under all possible environmental conditions. The phenotype may vary with changes in environment without a change in the genotype of the plant.

DETAILED PLANT DESCRIPTION

Figure 1:
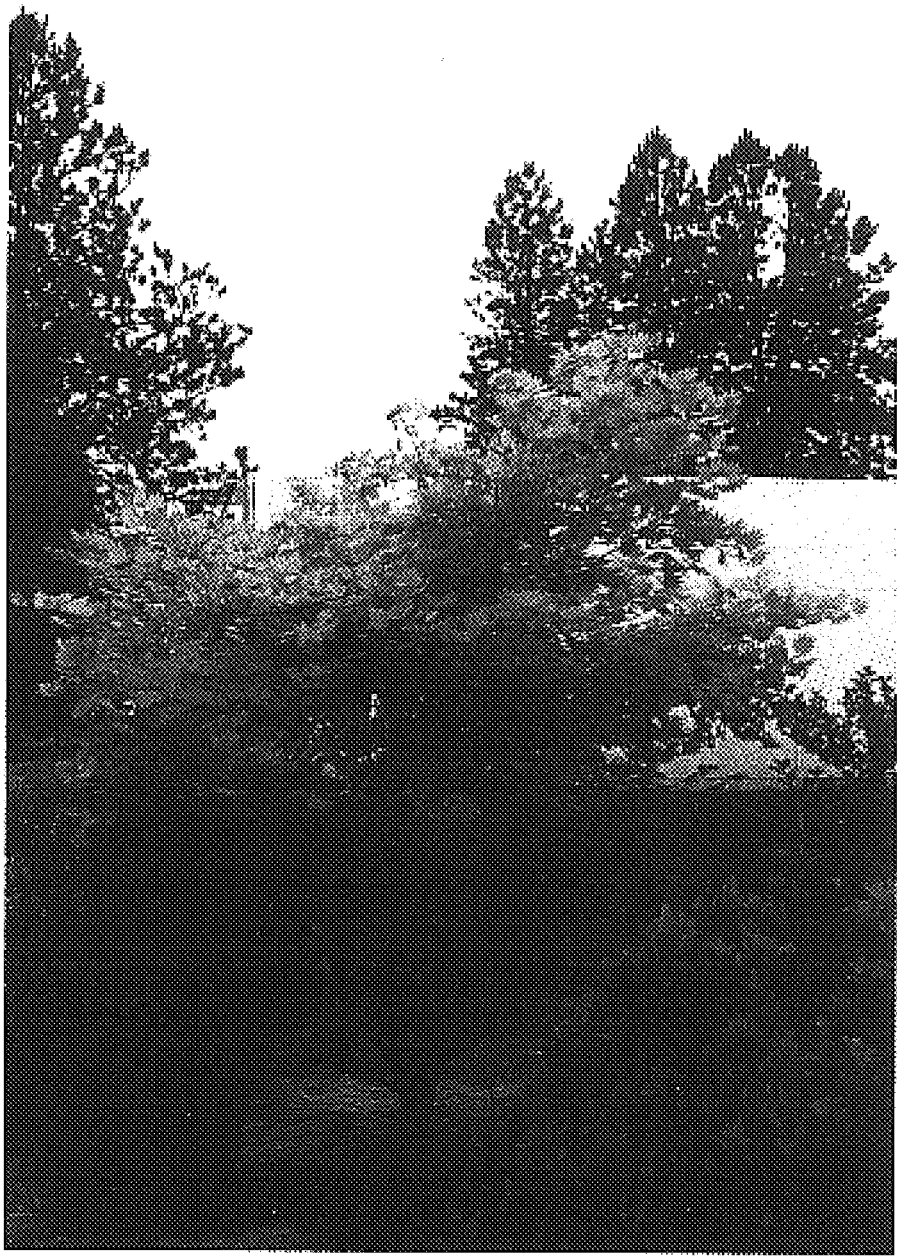
FIG. 1 shows the mature 17 year old plant growing in the ground in Brooks, Oreg. No fertilizer was used to stimulate the growth rate. Picture taken in early July 2004 under partly cloudy conditions.
Figure 2:
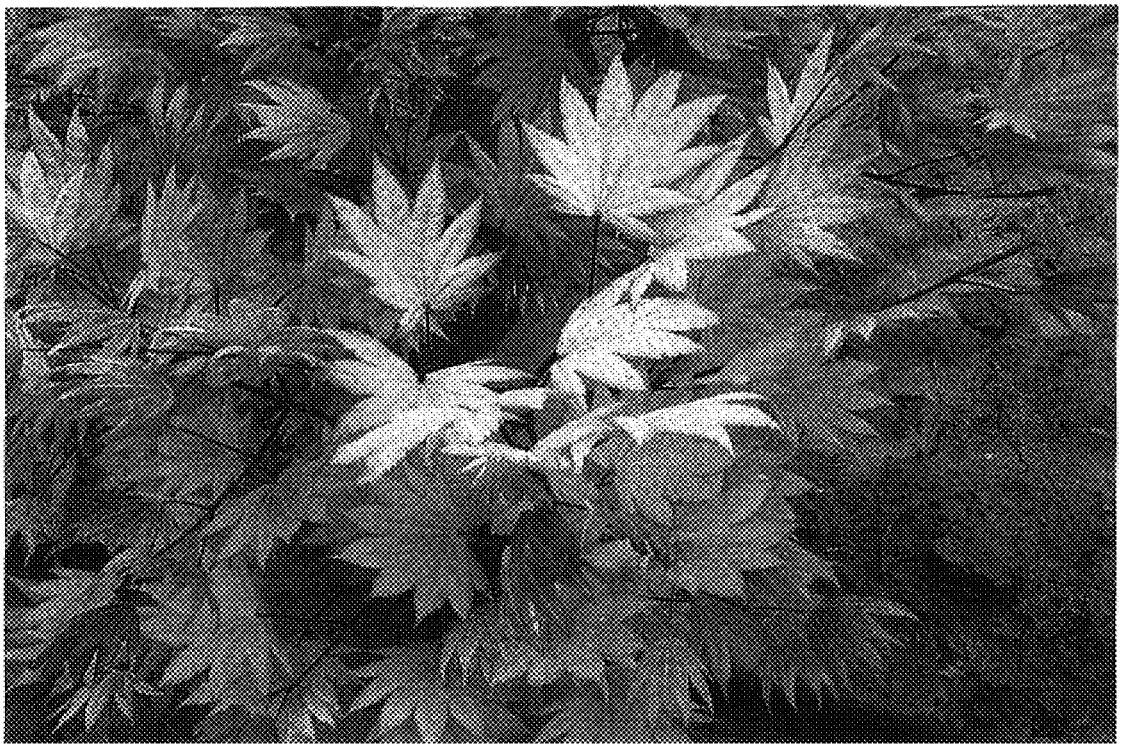
FIG. 2 shows a close up of a summer branch and foliage of a 4 year old plant grown in a cultivated field in Brooks, Oreg. Liquid feed 10-02-04 used to stimulate growth. Picture taken in late June 2004 under cloudy conditions.
Figure 3:
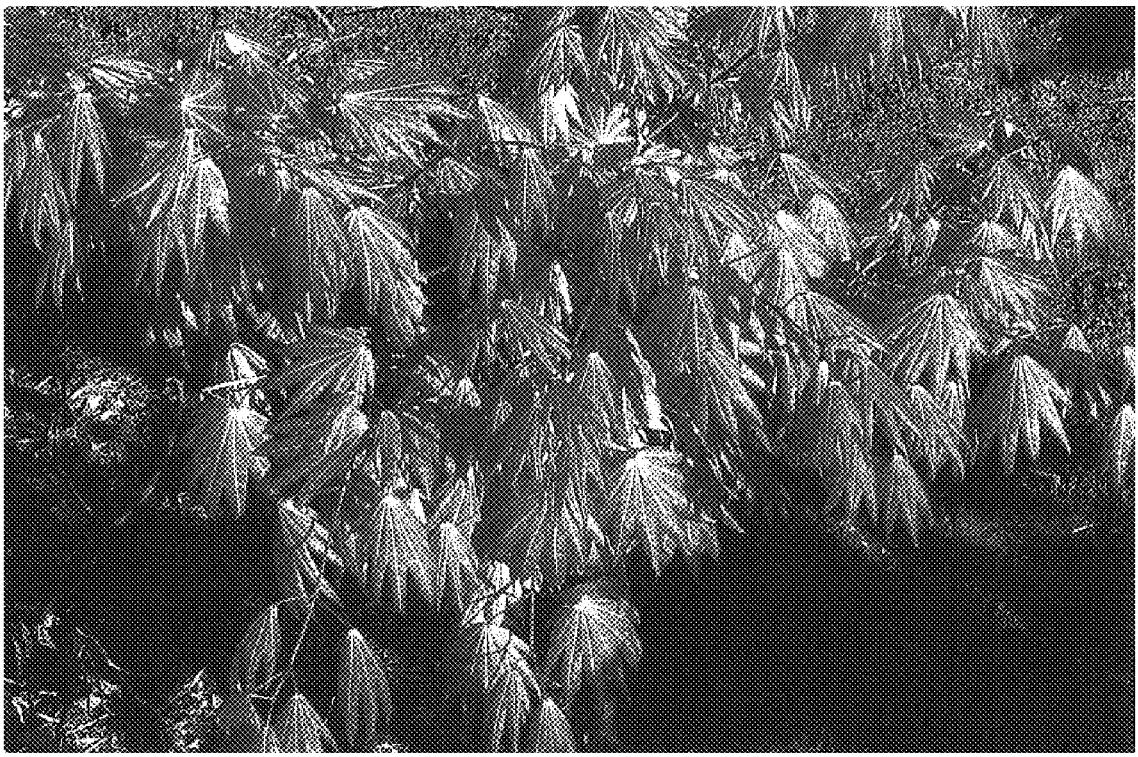
FIG. 3 shows the emerging new spring leaf color of a 4 year old plant in Brooks, Oreg. Picture taken in early May 2004 under sunny conditions.
Figure 4:
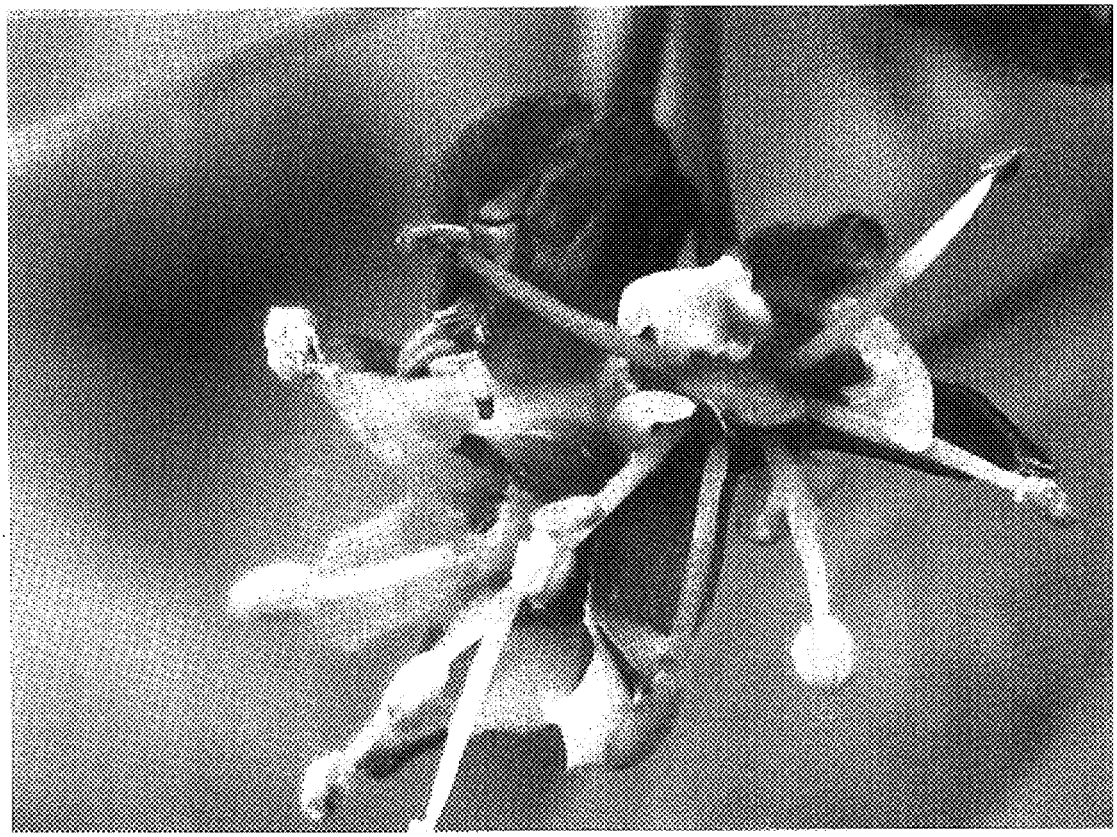
FIG. 4 shows a close up of the flowers of 17 the year old plant grown in Brooks, Oreg. Picture taken in early April 2004 under cloudy conditions.

The following is a detailed description of the new cultivar based on observations taken in early July of 2004 of a four-year-old specimen grown in the ground in full sun in Brooks, Oreg. The flower and fruit data are from branches of a 17 year old plant grown in the same manner. The color descriptions are all based on The Royal Horticultural Society Colour Chart.

The plants were grown in cultivated field in Brooks, Oreg. under drip irrigation. The 17 year old plant received no fertilizer, while the 4 year old tree received 10-02-04 liquid fertilizer to stimulate growth. Brooks, Oreg. is in zone 8A on the hardiness zone map. The average annual daily maximum temperature is 63.2° F. and the average annual daily minimum temperature is 41.0° F. The average annual rain fall is typically 40"–60".

Plant:
*Type.*—Deciduous tree.
*Hardiness.*—USDA Zones 5 to 7.
*Size.*—Mature size unknown (17 year old tree has grown to about 4 meters tall and 3.5 meters wide).
*Form.*—Globose.
*Growth.*—Vigorous, typical four year old plants grown in Brooks, Oreg., exhibited about 90 cm growth in the leader and primary side branches during the 2004 growing season through the 1st of July 2004.

Branches: Observations of 4 year old plants show dense branching with main branches typically of 0.5 cm to 1 cm in diameter, typical branch spacing of 4.5 cm to 5.5 cm apart. Typical observed branching crouch angle is from 35 to 40 degrees from the main trunk. Average branch density on observed plants can range from 35 to 70 branches on 4 year old plants.

Stem:
*Type.*—Woody.
*Size.*—Trunk base of four year old specimens had a caliper that is 2.3 cm to 3.2 cm (caliper measured one inch above ground).
*Surface.*—Young stems are glabrous. Two year old stems have 0.5 mm lenticels. Lenticels increase in size with age.
*Color.*—This years' growth is Greyed-Orange 175A in the sun and Yellow-Green 146B in the shade. Last years' growth is Yellow-Green 146B with lenticels of Brown 199B to Grey 198D. Three year old stems are striated Brown 199B and Grey 198D. The trunk bark color is closest to 197A.

Leaf:
*Type.*—Simple.
*Shape.*—Orbicular.
*Arrangement.*—Opposite.
*Lobing.*—Each leaf has from 7 to 11 lobes, parted down one-third to one-half to the leaf base. Lobes ovate, attenuate.
*Margins.*—Doubly serrate.
*Apex.*—Attenuate.
*Base.*—Cordate.
*Venation.*—Palmate.
*Length.*—Grows to 10 cm.
*Width.*—Grows to 10 cm.
*Surface texture.*—Glabrous (just unfolding leaves pubescent).
*Surface.*—Matte.
*Texture.*—Papery.
*Petiole length.*—Typically 3.5 cm to 5.5 cm.
*Petiole texture.*—Glabrous.
*Petiole color.*—Greyed-Purple 185A on new leaves to Greyed-Red 178A on older leaves.
*Color.*—Topside — Emerges a brilliant carmine, Red-Purple 64B which darkens to Greyed-Red 178A with yellow green veins, Yellow-Green 151A. These mature to yellow in the hot sun, Yellow 11A. Shade leaves are Lime-Green, between Yellow-Green 145A and 144B with red edges and tips, Greyed-Red 181A. Bottom side — Spring, Grey-Brown 199A with veins of Yellow-Green 151A. Summer, Yellow-Green 146D to 145A with areas of Yellow 11A.

Inflorescence:
*Type.*—Terminal panicle.
*Number of flowers.*—5 to 8.
*Peduncle.*—Length — 3.5 cm. Diameter — 1 mm near. Color — Greyed-Purple 185A. Surface texture — Glandular pubescent.
*Pedicel.*—Length — 10 to 15 mm. Vestiture — Glabrous. Color — Greyed-Purple 185A.
*Bloom period.*—April in Brooks, Oreg.

Flower bud:
*Size.*—4 mm wide and 6 mm long.
*Description.*—Ovoid.
*Color.*—Greyed-Purple 185A.

Flower: Flowers (and seed) have been observed on plants as early as three years after grafting.
*Type.*—Perfect.
*Shape.*—Rotate.
*Size.*—6 mm deep and 10 mm wide.
*Petal count.*—5.
*Petal color.*—Pink, Red-Purple 69A, on upper and lower surfaces.
*Petal description.*—Ovate, undulate, 4.5 mm long and 3 mm wide.
*Calyx.*—5 sepals, Greyed-Purple 185A, 5 mm long and 3 mm wide.
*Stamen number.*—5.
*Stamen color.*—Yellow-Green 1A.
*Pollen color.*—Yellow 11D.
*Pollen production.*—Light to moderate.
*Pistil color.*—White 155A.
*Fragrance.*—None.

Fruit:
*Type.*—Two one-seeded samaras, fused at the ovary, shaped like dragonfly wings.
*Color.*—Yellow-Green 145A with samaras edged Greyed-Orange 174A.
*Size.*—3.5 cm long and 8 mm wide.

Seed:
*Shape.*—Ovoid.
*Size.*—5 mm long.
*Color.*—Brown 200A.

Seed set can very form light to moderate. Seeds observed have swollen ovaries.

Pest and Disease Tolerance: *Acer shirasawanum* 'MUNN 001' is a more vigorous grower than *Acer shirasawanum* 'Aureum'. Aphids and scale are known *Acer* problems. They have not been a problem for this cultivar on the seventeen year old specimen or on the vegetatively propagated material grown in Brooks, Oreg.

COMPARISONS TO SIMILAR *ACER*

Compared to *Acer shirasawanum* 'Aureum' (an unpatented plant), this new cultivar grows more than twice as fast. The new plant is easier to propagate from grafts, is more sun tolerant and less gold overall. The new cultivar has chartreuse to lime colored leaves in the summer rather than yellow. The new growth of *Acer shirasawanum* 'MUNN 001' is carmine to red rather than yellow.

I claim:

1. A new and distinct cultivar of *Acer shirasawanum* plant as shown and described, characterized by its striking carmine to red spring leaves, yellow to lime summer leaves, and vigorous growth rate.

* * * * *